United States Patent
Herfert et al.

(10) Patent No.: US 7,528,291 B2
(45) Date of Patent: May 5, 2009

(54) COLOR-STABLE SUPERABSORBENT POLYMER COMPOSITION

(75) Inventors: Norbert Herfert, Charlotte, NC (US); Michael M. Azad, Charlotte, NC (US); Peter W. Carrico, West Point, MS (US)

(73) Assignee: BASF Aktiengesellschaft, Ludwigshafen (DE)

( * ) Notice: Subject to any disclaimer, the term of this patent is extended or adjusted under 35 U.S.C. 154(b) by 570 days.

(21) Appl. No.: 10/547,452

(22) PCT Filed: Mar. 19, 2004

(86) PCT No.: PCT/EP2004/002878

§ 371 (c)(1),
(2), (4) Date: Aug. 29, 2005

(87) PCT Pub. No.: WO2004/085496

PCT Pub. Date: Oct. 7, 2004

(65) Prior Publication Data

US 2006/0252913 A1  Nov. 9, 2006

Related U.S. Application Data

(60) Provisional application No. 60/457,746, filed on Mar. 26, 2003.

(51) Int. Cl.
*A61F 13/49* (2006.01)
*C08J 3/28* (2006.01)
*C08F 2/16* (2006.01)

(52) U.S. Cl. .......................... 604/372; 522/42; 522/84; 522/86; 522/152; 522/153; 522/154; 524/815; 524/827; 524/831; 524/832; 428/402

(58) Field of Classification Search .................... 522/42, 522/84, 152, 153, 154, 86; 524/815, 827, 524/831, 832; 604/358, 372; 523/300; 428/402
See application file for complete search history.

(56) References Cited

U.S. PATENT DOCUMENTS

| | | | |
|---|---|---|---|
| 5,599,335 A | 2/1997 | Goldman et al. | 604/368 |
| 5,669,894 A | 9/1997 | Goldman et al. | 604/368 |
| 5,837,789 A | 11/1998 | Stockhausen et al. | 526/320 |
| 2002/0188036 A1 | 12/2002 | Flisher et al. | 522/86 |
| 2004/0077744 A1 | 4/2004 | Naylor et al. | 522/150 |

FOREIGN PATENT DOCUMENTS

| | | |
|---|---|---|
| DE | 41 23 889 | 3/1992 |
| DE | 196 46 484 | 5/1997 |
| EP | 290814 | 11/1988 |
| WO | 00/55245 | 9/2000 |
| WO | 01/25289 | 4/2001 |
| WO | 01/55228 | 8/2001 |

OTHER PUBLICATIONS

International Preliminary Report on Patentability in PCT/EP2004/002878.
International Search Report in PCT/EP2004/002878 dated Aug. 23, 2004.

*Primary Examiner*—Fred M Teskin
(74) *Attorney, Agent, or Firm*—Marshall, Gerstein & Borun LLP

(57) ABSTRACT

A color-stable superabsorbent polymer having long-term color stability, and methods of manufacturing the polymer, are disclosed. The color-stable superabsorbent polymer is prepared in the essential absence of a persulfate, and is subjected to a low dose of ultraviolet radiation. The resulting superabsorbent polymer resists color degradation during periods of extended storage, even at an elevated temperature and humidity.

27 Claims, No Drawings

COLOR-STABLE SUPERABSORBENT POLYMER COMPOSITION

CROSS-REFERENCE TO RELATED APPLICATION

This is the U.S. national phase application of International Application No. PCT/EP2004/002878, filed Mar. 19, 2004, which claims the benefit of U.S. provisional patent application Ser. No. 60/457,746, filed Mar. 26, 2003.

FIELD OF THE INVENTION

The present invention relates to superabsorbent polymers (SAPs) having long-term color stability, and to methods of preparing the color-stable SAPs. More particularly, the present invention relates to methods of preparing a color-stable SAP using a monomer mixture containing a polymerization initiator that is essentially free of a persulfate, and subjecting the resulting SAP hydrogel to a low dose of UV radiation. The color-stable SAP can be incorporated into articles, such as bandages, diapers, sanitary napkins, and other absorbent products, wherein the SAP retains a clean, white color during extended storage periods, even under high temperature and humidity conditions.

BACKGROUND OF THE INVENTION

Water-absorbing resins are widely used in sanitary and hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidones, and polyacrylonitriles.

Such water-absorbing resins are termed "superabsorbent polymers," or SAPs, and typically are lightly crosslinked hydrophilic polymers. SAPs are discussed generally in U.S. Pat. Nos. 5,669,894 and 5,559,335, each incorporated herein by reference. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, such as a diaper.

As used herein, the term "SAP particles" refers to superabsorbent polymer particles in the dry state, more specifically, particles containing from no water up to about 10%, by weight, water. The terms "SAP gel," "SAP hydrogel," or "hydrogel" refer to a superabsorbent polymer containing at least about 10%, by weight, water, and often, particles that have absorbed at least their weight in water, and typically several times their weight in water.

SAPs have a tendency to degrade in color after long periods of storage. The tendency of an SAP to undergo a color transition from a clean, crisp, white color to a honey brown color accelerates as storage time, temperature, and humidity increase. In temperate climates, such as the United States and Europe, the rate at which an SAP undergoes color degradation is sufficiently slow such that the SAP, or article containing the SAP, typically is consumed before a color change is observable to the naked eye.

However, in tropical and subtropical climates, such as in South America and Southeast Asia, SAP color degradation is sufficiently rapid such that a color change often occurs before the SAP, or article containing the SAP, is consumed. In areas like Southeast Asia, an SAP can change color from white to honey brown in about 4 to 6 weeks. This problem is exacerbated because the SAPs may be produced far from the tropical climate, thereby increasing the time span from SAP production to use. Furthermore, consumption of articles containing an SAP in such climates is relatively low, therefore further increasing the time period between SAP production and use.

The change in color of the SAP does not affect SAP performance, but adversely affects consumer acceptance of articles containing the color-degraded SAPs. In particular, consumers observing a color-degraded SAP in a diaper form an opinion that the diaper contains a contaminant, is somehow soiled or faulty, or is of low quality. The diaper typically is returned for a refund, and the consumer is less likely to repurchase that brand of diaper.

Problems also arise at the manufacturing level because manufacturers of diapers and other articles containing an SAP refuse to incorporate a discolored SAP into their products, and return the discolored SAP to the SAP manufacturer. A color-degraded SAP, therefore, ultimately adversely affects the manufacturer of articles and the manufacturer of the SAP, who must absorb the cost of the returned goods.

It would be desirable to provide an SAP that exhibits exceptional color stability properties, such that the SAP retains its crisp, white color throughout the useful life of the SAP, or an article containing the SAP, even when stored under high temperature and humidity conditions. Furthermore, it would be desirable to provide an SAP having a long-term color stability and low residual monomer content, without adversely affecting the absorbent properties of the SAP, such as absorbing a large amount of liquids quickly, having a good fluid permeability into and through the SAP, and having a high gel strength, such that an SAP hydrogel formed from the SAP does not deform or flow under an applied stress or pressure.

Currently, SAPs, like partially neutralized, lightly crosslinked, polyacrylic acid, are manufactured using a persulfate as a component of the polymerization initiator system. A persulfate is included in the initiator system as the oxidizing agent of a redox initiator pair and to reduce the amount of residual acrylic acid monomer in the SAP to acceptable levels. A persulfate also can act as a thermal initiator. However, a persulfate interacts with the MEHQ inhibitor present in acrylic acid monomer and imparts a low initial color to the SAP. This low initial SAP color progresses to a severe SAP discoloration over time, and especially under high temperature and humidity conditions.

The present invention is directed to overcoming the problem of SAP discoloration attributed to the presence of a persulfate in the preparation of an SAP. As discussed in detail hereafter, the present invention overcomes the SAP discoloration problem by essentially omitting a persulfate from the polymerization initiator system of a monomer mixture, and by subjecting the SAP hydrogel resulting from the polymerization to a low dose of ultraviolet (UV) radiation.

Ultraviolet radiation previously has been used in the preparation of SAPs. For example, UV radiation has been used in conjunction with a photoinitiator to initiate polymerization of monomers to form an SAP hydrogel, as disclosed in EP 0 290 814 B1. DE 41 23 889 A1 discloses UV irradiation of a water-absorbing resin prepared from a water-soluble polymer and a polysaccharide and/or crosslinking agent, in the presence of a radical scavenger, to provide a water-absorbing resin having a low amount of water-soluble components (7 wt % or less) and a low amount of residual monomer (500 ppm or less). The UV radiation is applied during drying or crushing of the water-absorbing resin.

PCT publication WO 01/55228 discloses subjecting a water-soluble or water-swellable polymer to UV radiation to reduce residual monomer content. An ultraviolet initiator is used in an amount of up to 10,000 ppm, by weight of monomers, preferably up to 5000 ppm, more preferably 50 to 3,000 ppm, and still more preferably 500 to 2,000 ppm. UV radiation typically is conducted for about 20 minutes.

PCT publication WO 01/25289 discloses subjecting an acrylic polymer to UV radiation after, or simultaneously with, comminuting a gelled polymer to gelled polymer particles. In particular, the comminuted gel particles can be irradiated during a drying step in a fluid bed dryer.

SUMMARY OF THE INVENTION

The present invention is directed to a superabsorbent polymer (SAP) having long-term color stability, and to methods of manufacturing a color-stable SAP composition. More particularly, the present invention is directed to a method of preparing a color-stable SAP, without adversely affecting other fluid absorption and retention properties of the SAP particles, by essentially omitting a persulfate from the polymerization initiator system, and subjecting the SAP hydrogel resulting from the polymerization to a low dose of UV radiation. A color-stable SAP prepared by the present method retains a crisp, clean white color over an extended storage period at a high temperature and humidity, i.e., at least 30 days when stored at 60° C. and 90% relative humidity.

One aspect of the present invention, therefore, is to provide a method of manufacturing a color-stable SAP, including the steps of (a) polymerizing a monomer mixture comprising (i) a monomer that provides an SAP, like an $\alpha,\beta$-unsaturated carboxylic acid, such as acrylic acid, either neutralized, unneutralized, or partially neutralized, (ii) a crosslinking agent, (iii) an initiator system that is essentially free of a persulfate, and (iv) a photoinitiator, to form an SAP hydrogel containing about 25 wt % or less water, (b) subjecting the SAP hydrogel to a low dose of UV radiation, and (c) then drying the irradiated SAP hydrogel to provide a color-stable SAP. The resulting color-stable SAP has a low residual monomer content and maintains a crisp white color over an extended time, even under high temperature and humidity storage conditions.

Another aspect of the present invention is to provide a method of manufacturing a color-stable SAP including the steps of polymerizing a monomer mixture that provides an SAP, for example, a polymerized $\alpha,\beta$-unsaturated carboxylic acid, to form an SAP hydrogel containing about 25 wt % or less water, subjecting the SAP hydrogel to UV radiation for about 1 to about 60 minutes, comminuting the irradiated SAP hydrogel to form irradiated SAP hydrogel particles, then drying the irradiated SAP hydrogel particles to form irradiated color-stable SAP particles. In accordance with an important feature of the present invention, the SAP hydrogel is subjected to a low dose of UV radiation, i.e., about 5 to about 2000 milliwatts (mW) of UV radiation per square centimeter ($cm^2$) of SAP hydrogel. In accordance with another important feature of the present invention, the polymerization reaction is performed without the assistance of a UV radiation dose.

Accordingly, the photoinitiator is still present after the polymerization, when the SAP hydrogel is subjected to a low dose UV radiation.

In preferred embodiments, the monomer mixture comprises (a) an $\alpha,\beta$-unsaturated carboxylic acid, (b) a crosslinking agent, (b) a polymerization initiator system that is essentially free of a persulfate, (d) a photoinitiator in an amount of about 10 to about 1000 ppm by weight of $\alpha,\beta$-unsaturated carboxylic acid and crosslinking agent, and (e) water. After drying, the color-stable SAP particles optionally are surface treated to provide surface crosslinks on the color-stable SAP particles.

Yet another aspect of the present invention is to incorporate the color-stable SAP particles into articles used to absorb liquids, for example, a diaper, a catamenial device, a feminine hygiene product, an adult incontinence product, general purpose wipes and cloths, and similar absorbent products. The articles resist color degradation over the expected life of the article, even in high temperature and humidity climates.

The above and other aspects and advantages of the present invention will become apparent from the following detailed description of the preferred embodiments of the invention, taken in conjunction with the examples and the claims.

DETAILED DESCRIPTION OF THE INVENTION

The present invention is directed to SAPs having a long-term color stability, and to methods of preparing the color-stable SAPs. The color-stable SAPs exhibit only a minor color change, to the naked eye, after storage for 30 days at 60° C. and 90% relative humidity. The present SAPs are prepared from a monomer mixture that is essentially free of a persulfate, and the SAP hydrogel resulting from polymerizing the monomer mixture is subjected to a low dose of UV radiation, which, in combination, impart color stability to the SAP and reduce the amount of residual monomer in the SAP.

SAPs are manufactured by a number of polymerization techniques, including modified bulk polymerization. In modified bulk polymerization, SAPs are prepared from an aqueous mixture containing a relatively high concentration monomers and one or more crosslinking agents to provide a water-absorbent, but water-insoluble, polymer. The aqueous monomer mixture also contains polymerization initiators, including a persulfate, like sodium persulfate. A persulfate has been considered an important or essential polymerization initiator ingredient in order to reduce residual acrylic acid monomer content in SAP particles to acceptable levels.

In the typical manufacture of an SAP, the SAP is neutralized at least about 15 mole percent, more preferably at least about 50 mole percent, and usually about 70 to about 80 mole percent, to achieve optimum absorbency. Neutralization can be achieved by neutralizing the monomers before polymerization, or the polymer can be neutralized after the polymerization reaction is substantially complete.

As used herein, a modified bulk polymerization process is defined as a polymerization process wherein a significant amount of water from the aqueous mixture of monomers is removed during polymerization by the heat of reaction. A modified bulk polymerization process yields a relatively dry SAP hydrogel, i.e., a water content of about 25 wt % or less, without an additional drying step.

After polymerization and internal crosslinking of the monomers, including by partial neutralization, e.g., about 15 to about 100 mole percent neutralization, preferably about 50 to about 80 mole percent neutralization, the polymer is comminuted, e.g., shredded or chopped, then dried, if necessary, and milled to a desired particle size. The polymer preferably then is surface treated. In embodiments wherein surface treatment is employed, a surface crosslinking agent typically is applied to the dried SAP particles. Generally, after application of the surface crosslinking agent, the SAP particles then are subjected to conditions wherein the surface crosslinking agent reacts with a portion of the SAP to crosslink the surfaces of the SAP particles.

In one embodiment of the present invention, a color-stable SAP is prepared by a method comprising the steps of (a) polymerizing a monomer mixture comprising (i) a monomer capable of providing an SAP polymer, like an α,β-unsaturated carboxylic acid, such as acrylic acid, either neutralized, unneutralized, or partially neutralized, (ii) a crosslinking agent, (iii) a polymerization initiator that is essentially free of a persulfate, (iv) a photoinitiator, and (v) water, to form an SAP hydrogel containing about 25 wt % or less water, (b) subjecting the SAP hydrogel to a low dose of UV radiation, (c) then comminuting the irradiated SAP hydrogel to form irradiated SAP hydrogel particles, (d) drying the resulting irradiated SAP hydrogel particles, and (e) optionally surface treating the color-stable SAP particles.

The present color-stable SAPs are based on polymerized vinyl monomers, particularly α,β-unsaturated carboxylic acids, that, after polymerization, have the ability to absorb several times their weight of a liquid when crosslinked. The remainder of the specification is directed to a color-stable SAP based on acrylic acid, however, other vinyl monomers, like (meth)acrylonitrile or a (meth)acrylamide, or an ethylenic monomer having an amine substituent or a precursor to an amine substituent, e.g., N-vinyl acetamide, and other α,β-unsaturated carboxylic acids and anhydrides, also can be used in the manufacture of color-stable SAPs of the present invention. The color-stable SAPs prepared by the present methods exhibit improved color stability regardless of the identity of the monomers used to prepare the SAP, and particularly SAPs based on an α,β-unsaturated carboxylic acid or anhydride.

Accordingly, the chemical makeup of the color-stable SAP is not limited. The color-stable SAPs, therefore, can comprise an acidic water-absorbing resin (i.e., an anionic SAP), a basic water-absorbing resin (i.e., a cationic SAP), or a multicomponent SAP particle as disclosed in U.S. Pat. Nos. 6,072,101; 6,159,591; 6,222,091; and 6,329,062, each incorporated herein by reference. An extensive list of suitable SAP-forming monomers can be found in U.S. Pat. Nos. 4,076,663 and 5,149,750, each incorporated herein by reference.

Generally, acidic SAPs have carboxylate, sulfonate, sulfate, and/or phosphate groups incorporated along the polymer chain. Polymers containing these acid moieties are synthesized either from monomers previously substituted with one or more of these acidic functional groups or by incorporating the acidic functional group into the polymer after synthesis. To incorporate carboxyl groups into a polymer, any of a number of ethylenically unsaturated carboxylic acids can be homopolymerized or copolymerized. Carboxyl groups also can be incorporated into the polymer chain indirectly by hydrolyzing a homopolymer or copolymer of monomers such as acrylamide, acrylonitrile, methacrylamide, and alkyl acrylates or methacrylates. An acidic SAP can be either a strong or a weak acidic water-absorbing resin, and can be a homopolymer or a copolymer.

The acidic SAP typically is a neutralized, lightly crosslinked acrylic-type resin, such as neutralized, lightly crosslinked polyacrylic acid. The lightly crosslinked acidic SAP typically is prepared by polymerizing an acidic monomer containing an acyl moiety, e.g., acrylic acid, or a moiety capable of providing an acid group, i.e., acrylonitrile, in the presence of a crosslinking agent, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic SAP contains at least 50%, and more preferably, at least 75%, and up to 100%, acidic monomer units. The acidic resin can be unneutralized or neutralized, preferably neutralized at least 50 mole %, and most preferably at least 70 mole %, with a base prior to drying.

Ethylenically unsaturated carboxylic acid monomers, and anhydrides, amides, esters, and salts thereof, useful in the acidic SAP include, but are not limited to, acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, 2-methyl-2-butene dicarboxylic acid, maleamic acid, N-phenyl maleamide, maleamide, maleic anhydride, fumaric anhydride, itaconic anhydride, citraconic anhydride, mesaconic anhydride, methyl itaconic anhydride, ethyl maleic anhydride, diethyl maleate, methyl maleate, and maleic anhydride.

Sulfonate-containing acidic SAPs can be prepared from monomers containing functional groups hydrolyzable to the sulfonic acid form, for example, alkenyl sulfonic acid compounds and sulfoalkyl acrylate compounds. Ethylenically unsaturated sulfonic acid monomers include, but are not limited to, aliphatic or aromatic vinyl sulfonic acids, such as vinylsulfonic acid, allylsulfonic acid, vinyltoluene sulfonic acid, styrenesulfonic acid, acrylic and methacrylic sulfonic acids, such as sulfoethyl acrylate, sulfoethyl methacrylate, sulfopropyl acrylate, 2-vinyl-4-ethylbenzenesulfonic acid, 2-allylbenzenesulfonic acid, 1-phenylethylene sulfonic acid, sulfopropyl methacrylate, 2-hydroxy-3-methacryloxypropyl sulfonic acid, and 2-acrylamide-2-methylpropane sulfonic acid.

Sulfate-containing acidic SAPs are prepared by reacting homopolymers or copolymers containing hydroxyl groups or residual ethylenic unsaturation with sulfuric acid or sulfur trioxide. Examples of such sulfated polymers include sulfated polyvinyl alcohol, sulfated hydroxyethyl acrylate, and sulfated hydroxypropyl methacrylate. Phosphate-containing acidic SAPs are prepared by homopolymerizing or copolymerizing ethylenically unsaturated monomers containing a phosphoric acid moiety, such as methacryloxy ethyl phosphate.

The acidic SAP, either strongly or weakly acidic, can be any resin that acts as an SAP in its neutralized form. Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly(vinylphosphoric acid), poly(vinylsulfuric acid), sulfonated polystyrene, poly(aspartic acid), poly(lactic acid), and mixtures thereof. The preferred acidic resins are the polyacrylic acids.

The acidic SAP contains 0 to 100 percent neutralized pendant carboxylate groups (i.e., DN=0 to DN=100). Neutralization of carboxylic acid groups is accomplished using a strong organic or inorganic base, such as sodium hydroxide, potassium hydroxide, ammonia, ammonium hydroxide, or an organic amine.

Analogous to the acidic SAP, a color-stable basic SAP can be manufactured by the present method. The basic SAP can be a strong or weak basic water-absorbing resin. The strong basic resins typically are present in the hydroxide (OH) or bicarbonate ($HCO_3$) form. The basic SAP can be a single resin or a mixture of resins. The basic SAP can be a homopolymer or a copolymer.

The basic SAP, either strongly or weakly basic, therefore, can be any resin that acts as an SAP in its charged form. The basic SAP typically is a lightly crosslinked resin, such as a lightly crosslinked polyethylenimine, a poly(allylamine), a poly(allylguanidine), a poly(dimethyidiallylammonium hydroxide), a quaternized polystyrene derivative, a guanidine-modified polystyrene, a poly(vinylguanidine), or a poly(dialkylaminoalkyl(meth)acrylamide) prepared by polymerizing and lightly crosslinking a monomer having the structure

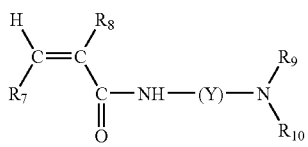

or its ester analog

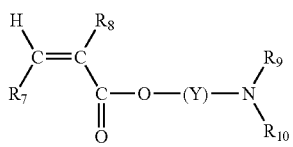

wherein $R_7$ and $R_8$, independently, are selected from the group consisting of hydrogen and methyl, Y is a divalent straight chain or branched organic radical having 1 to 8 carbon atoms, $R_9$ is hydrogen, and $R_{10}$ is hydrogen or an alkyl radical having 1 to 4 carbon atoms. Preferred basic SAPs include a poly(vinylamine), polyethylenimine, poly(vinylguanadine), poly(methylaminoethyl acrylamide), and poly(methylaminopropyl methacrylamide). Basic SAPs are disclosed in U.S. Pat. No. 6,159,591, incorporated herein by reference. The lightly crosslinked basic SAP can contain other copolymerizable units and is crosslinked using a polyfunctional organic compound, as set forth above with respect to the acidic SAP.

Copolymerizable monomers for introduction into an acidic SAP or a basic SAP include, but are not limited to, ethylene, propylene, isobutylene, $C_{1-4}$ alkyl acrylates and methacrylates, vinyl acetate, methyl vinyl ether, and styrenic compounds having the formula:

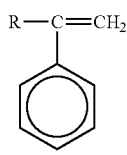

wherein R represents hydrogen or a $C_{1-6}$ alkyl group, and wherein the phenyl ring optionally is substituted with one to four $C_{1-4}$ alkyl or hydroxy groups.

Suitable $C_{1-4}$ alkyl acrylates include, but are not limited to, methyl acrylate, ethyl acrylate, isopropyl acrylate, n-propyl acrylate, n-butyl acrylate, and the like, and mixtures thereof. Suitable $C_{1-4}$ alkyl methacrylates include, but are not limited to, methyl methacrylate, ethyl methacrylate, isopropyl methacrylate, n-propylmethylmethacrylate, n-butyl methacrylate, and the like, and mixtures thereof or with $C_{1-4}$ alkyl acrylates. Suitable styrenic compounds include, but are not limited to, styrene, α-methylstyrene, p-methylstyrene, t-butyl styrene, and the like, and mixtures thereof or with $C_{1-4}$ alkyl acrylates and/or methacrylates.

As previously stated, the present invention is not limited to SAPs based on acrylic acid, but preferably extends to SAPs prepared for α,β-unsaturated carboxylic acids including, but not limited to, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, and maleic anhydride. Acrylic acid, i.e., $CH_2=CHCO_2H$, is the most preferred α,β-unsaturated carboxylic acid.

Especially preferred SAPs prepared by the present method are the alkali metal acrylate SAPs obtained, for example, by copolymerizing 100 parts of a monomer mixture comprising about 1 to about 50 mole percent acrylic acid, about 50 to about 99 mole percent of an alkali metal acrylate, and about 0.1 to about 5 percent by weight of an internal crosslinking agent, in an aqueous solution containing at least about 20% and up to 100%, and preferably about 40% to about 80%, by weight, of monomers. This is a preneutralized monomer mixture. In another preferred embodiment, the alkali metal acrylate SAPs are obtained by first polymerizing acrylic acid, then neutralizing the SAP hydrogel with an alkali metal base, i.e., a postneutralization polymerization.

As set forth above, polymerization of acidic or basic monomers, and optional copolymerizable monomers, most commonly is performed by free radical processes in the presence of a polyfunctional crosslinking agent. The acidic and basic SAPs are crosslinked to a sufficient extent such that the SAP is water insoluble. Crosslinking renders the SAPs substantially water insoluble, and, in part, serves to determine the absorption capacity of the SAPs. For use in absorption applications, an acidic or basic SAP is lightly crosslinked, i.e., has a crosslinking density of less than about 20%, preferably less than about 10%, and most preferably about 0.01% to about 7%.

A crosslinking agent most preferably is used in an amount of less than about 7 wt %, and typically about 0.1 wt % to about 5 wt %, based on the total weight of monomers. Examples of crosslinking polyvinyl monomers include, but are not limited to, polyacrylic (or polymethacrylic) acid esters, represented by the following formula (I), and bisacrylamides, represented by the following formula (II).

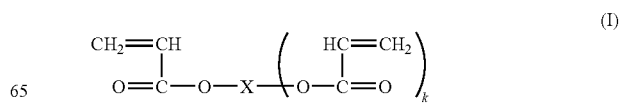

wherein X is ethylene, propylene, trimethylene, cyclohexylene, hexamethylene, 2-hydroxypropylene, —(CH$_2$CH$_2$O)$_p$CH$_2$CH$_2$—, or

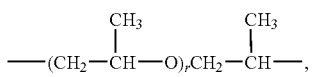

p and r each are an integer 5 to 40, and k is 1 or 2;

wherein l is 2 or 3.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacrylate, trimethylolpropane triacrylate, trimethylolpropane trimethacrylate, tris(2-hydroxyethyl)isocyanurate triacrylate, tris(2-hydroxyethyl)isocyanurate trimethacrylate, divinyl esters of a polycarboxylic acid, diallyl esters or a polycarboxylic acid, triallyl terephthalate, diallyl maleate, diallyl fumarate, hexamethylene bismaleimide, trivinyl trimellitate, divinyl adipate, diallyl succinate, a divinyl ether of ethylene glycol, cyclopentadiene diacrylate, tetraallyl ammonium halides, or mixtures thereof. Compounds such as divinylbenzene and divinyl ether also can be used as crosslinking agents. Especially preferred crosslinking agents are N,N'-methylenebisacrylamide, N,N'-methylenebismethacrylamide, ethylene glycol dimethacrylate, and trimethylolpropane triacrylate.

In the preparation of a color-stable SAP of the present invention, the monomers, for example, an α,β-unsaturated carboxylic acid, and especially, acrylic acid, and crosslinking agent are subjected to a polymerization reaction in the presence of a polymerization initiator. One or more polymerization initiator is added to the aqueous solution of the monomers and crosslinking agent to facilitate polymerization and formation of the SAP hydrogel.

Often the initiator comprises at least one thermal initiator and at least one redox initiator. Any of the various polymerization initiators that are known for use in preparing SAPs can be used in the present invention. However, in accordance with an important feature of the present invention, the polymerization initiator is essentially free of a persulfate. As used herein, the term "essentially free" is defined as the total concentration of persulfate of 0 ppm up to 300 ppm, by weight of the monomer mixture. In preferred embodiments, the polymerization inhibitor is free of a persulfate.

Examples of useful polymerization initiators are redox initiators comprising (a) a reducing agent, such as a sulfite or bisulfite of an alkali metal, ammonium sulfite, sodium metabisulfite, ammonium bisulfite, ascorbic acid, a sugar, an aldehyde, or a primary or secondary alcohol, and (b) an oxidizing agent, like hydrogen peroxide; an alkyl hydroperoxide, like t-butyl hydroperoxide; t-butyl perbenzoate; t-butyl peroxy isopropyl carbonate; 1,1-di-t-butylperoxy-3,3,5-trimethylcyclohexane; benzoyl peroxide, dicumyl peroxide; caprylyl peroxide; sodium peracetate; and other redox initiators known to persons skilled in the art. Preferred redox initiators are (a) 2-hydroxy-2-sulfinatoacetic acid and hydrogen peroxide, and (b) sodium sulfite or bisulfite and hydrogen peroxide, each used, for example, in an amount of about $2\times10^{-5}$ to about $2\times10^{-2}$ mole percent, based on moles of monomers (i.e., monomer and crosslinking agent) present in the monomer mixture. 2-Hydroxy-2-sulfinatoacetic acid in a pure form is available commercially from Brüggemann Chemical, Heilbron, Germany, as BRUGGOLITE® FF7. 2-Hydroxy-2-sulfinatoacetic acid, in combination with 2-hydroxy-2-sulfonatoacetic acid and sodium bisulfite, is available commercially from Brüggemann Chemical as BRUGGOLITE® FF6. Additional sulfinic acid derivatives useful as a reducing agent of the redox initiator in the present invention are disclosed in U.S. Pat. No. 6,211,400, incorporated herein by reference.

The redox initiators are used alone or in suitable combination with a thermal initiator. Examples of suitable thermal initiators are the "azo" initiators, including, but not limited to, azobisisobutyronitrile; 4-t-butylazo-4'-cyanovaleric acid; 4,4'-azobis(4-cyanovaleric acid); 2,2'-azobis(2-amidinopropane)dihydrochloride; 2,2'-azobis(2,4-dimethylvaleronitrile); dimethyl 2,2'-azobisisobutyrate; 2,2'-azodimethyl bis(2,4-dimethylvaleronitrile); (1-phenylethyl) azodiphenylmethane; 2,2'-azobis(2-methylbutyronitrile); 1,1'-azobis(1-cyclohexanecarbonitrile); 2-(carbamoylazo) isobutyronitrile; 2,2'-azobis(2,4,4-trimethylpenta-2-phenylazo-2,4-dimethyl-4-methoxyvaleronitrile; 2,2'-azobis(2-methylpropane); 2,2'-azobis(N,N'-dimethyleneisobutyramidine)dihydrochloride; 4,4'azobis (4-cyanopentanoic acid); 2,2'-azobis(2-methyl-N-[1,1-bis(hydroxymethyl)-2-hydroxyethyl]propionamide); 2,2'-azobis(2-methyl-N-[1,1-bis(hydroxymethyl)ethyl] propionamide); 2,2'-azobis[2-methyl-N-(2-hydroxyethyl) propionamide]; 2,2'-azobis(isobutyramide)dihydrate; and other thermal initiators known to persons skilled in the art.

Especially preferred polymerization initiators comprise (a) a redox initiator comprising (i) hydrogen peroxide as an oxidizing agent and 2-hydroxy-2-sulfinatoacetic acid, sodium bisulfite, sodium sulfite, or a mixture thereof as a reducing agent, and (b) an azo initiator, such as azobisisobutyronitrile and 2,2'-azobis(2-amidinopropane)dihydrochloride. A preferred thermal initiator for use in the present method is 2,2'-azobis(2-amidinopropane)dihydrochloride, commercially available under the tradename V-50 from Wako Chemicals U.S.A., Inc., Richmond, Va. The initiator typically is used in an aqueous solution, but the initiator can be diluted with another suitable solvent.

In addition to the polymerizable monomer, crosslinking agent, and polymerization initiator, a monomer mixture used in the method of the present invention contains a photoinitiator. The photoinitiator is present in the monomer mixture in a low amount, in particular, in an amount of about 10 to about 1000 ppm, by weight of monomers and crosslinking agent, and preferably about 15 to about 500 ppm. To achieve the full advantage of the present invention, the photoinitiator is present in the monomer mixture in an amount of about 20 to about 300 ppm, by weight of monomers and crosslinking agent.

The photoinitiator is present to assist in reducing the residual acrylic acid monomer in the SAP. In prior methods of manufacturing an SAP, a persulfate was utilized as a component of the redox initiator to initiate the polymerization reaction and to reduce the amount of residual acrylic acid monomer in the SAP. However, a persulfate interacts with the MEHQ inhibitor present in acrylic acid monomer and provides a slightly colored SAP. This color increases over time, and especially in hot, humid conditions, to provide an unacceptable, honey-brown colored SAP.

In accordance with an important feature of the present invention, the monomer mixture is essentially free of a persulfate. The photoinitiator, in combination with a low dose of UV radiation, then serves to reduce the amount of residual acrylic acid monomer in the SAP, i.e., to below 500 ppm by weight of the SAP, that previously was accomplished using a persulfate.

The identity of the photoinitiator is not limited, but is inert (i.e., is not decomposed) under polymerization conditions. A preferred photoinitiator has a structure

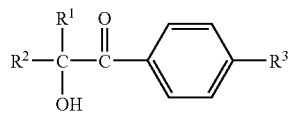

wherein $R^1$ and $R^2$, independently, are $C_{1-3}$ alkyl, or are taken together to form a $C_{4-8}$ carbocyclic ring, $R^3$ is H, methyl, ethyl, or $(OCH_2CH_2)_n OH$, and n is 1-20.

Specific photoinitiators include, but are not limited to,

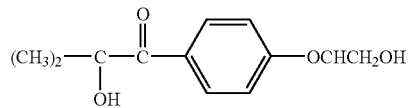

i.e., 1-[4-(2-hydroxyethyl)phenyl)-2-hydroxyl-2-methyl-1-propane-1-one, available as IRGACURE® 2959 from Ciba Specialty Chemicals, Hawthorne, N.Y.;

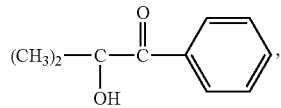

i.e., 1-phenyl-2-hydroxy-2-methyl-1-propane-1-one, also available from Ciba Specialty Chemicals as DAROCUR® 1173;

hydroxycyclohexyl phenyl ketone, available from Ciba Chemical Specialties as IRGACURE® 184;

2,2-dimethoxy-1,2-diphenylethan-1-one available from Ciba Chemical Specialties as IRGACURE® 651;

and mixtures thereof.

Additional useful photoinitiators include, but are not limited to, benzoin, benzoin ethers, benzyl ketals, acylphosphine oxides, camphorquinone, bisimidazole, a dialkylacetophenone, an α-aminoacetophenone, a chlorinated acetophenone, benzophenone, a benzophenone derivative (for example, p-benzoylbenzyl trimethyl ammonium bromide), a thioxanthone derivative (for example, (3-(3,4-dimethyl-9-oxo-9H-thioxanthen-2-yloxy)-2-hydroxypropyl)trimethyl ammonium chloride), and mixtures thereof.

In addition to the monomers, crosslinking agent, polymerization initiators, and photoinitiator, the monomer mixture contains water. Generally, the monomer mixture contains 0 to about 80 wt %, more preferably about 20 to about 60 wt %, water, by weight of the monomer mixture.

The monomers present in monomer mixture are crosslinked concurrently with aqueous solution polymerization to a sufficient extent such that the resulting SAP is water insoluble, but has an ability to absorb several times its weight in water to form an SAP hydrogel. In many cases, after comminuting and drying of the SAP hydrogel, the resulting SAP is surface treated. Surface treatment results in surface crosslinking of the SAP particles. Surface treating an SAP enhances the ability of the SAP to absorb and retain aqueous media under a load.

As understood in the art, a surface-treated SAP has a higher level of crosslinking in the vicinity of the surface than in the interior. As used herein, "surface" describes the outer-facing boundaries of the SAP particle. For porous SAP particles, exposed internal surfaces also are included in the definition of surface.

In general, surface treating is achieved by contacting an SAP with a solution of a surface crosslinking agent to wet the outer surfaces of the SAP particles. Surface crosslinking and drying of the SAP particles then are performed, preferably by heating at least the wetted surfaces of the SAP particles. Surface treating also can be achieved by "annealing" (i.e., heating) the SAP particles at a sufficient temperature for a sufficient time to provide surface crosslinks.

Typically, a solution of a surface crosslinking agent contains about 0.01% to about 4%, and preferably about 0.4% to about 2%, by weight, surface crosslinking agent in a suitable solvent, for example, water or an alcohol. The solution can be applied as a fine spray onto the surface of freely tumbling SAP particles at a ratio of about 1:0.01 to about 1:0.5 parts by weight SAP particles to solution of surface crosslinking agent. The surface crosslinker is present in an amount of 0.001% to about 5%, and preferably 0.005% to about 0.5%, by weight of the SAP particles. To achieve the full advantage of the present invention, the surface crosslinker is present in an amount of about 0.01% to about 0.4%, by weight.

The crosslinking reaction and drying of the surface-treated SAP particles are achieved by heating the surface-treated polymer at a suitable temperature, e.g., about 25° C. to about 200° C., and preferably about 105° C. to about 180° C. However, any other method of reacting the crosslinking agent to achieve surface crosslinking of the SAP particles, and any other method of drying the SAP particles, like microwave energy or the such, can be used.

Suitable surface crosslinking agents possess sufficient reactivity such that crosslinking occurs in a controlled fashion, preferably at a temperature of about 25° C. to about 180° C. Nonlimiting examples of suitable surface crosslinking agents include:

(a) polyhydroxy compounds, such as glycols and glycerol;
(b) metal salts;
(c) quaternary ammonium compounds;
(d) a multifunctional epoxy compound, for example, ethylene glycol diglycidyl ether, bisphenol A diglycidyl ether, and bisphenol F diglycidyl ether;
(e) an alkylene carbonate, such as ethylene carbonate or propylene carbonate;
(f) a polyaziridine, such as 2,2-bishydroxymethyl butanol tris[3-(1-aziridine propionate)];
(g) a haloepoxy, such as epichlorohydrin;

(h) a polyamine, such as ethylenediamine;
(i) a polyisocyanate, such as toluene diisocyanate, isophorone diisocyanate, methylene diisocyanate, xylene diisocyanate, and hexamethylene diisocyanate;
(j) dihalides and disulfonate esters, for example, compounds of the formula Y—$(CH_2)_p$—Y, wherein p is a number from 2 to 12, and Y, independently, is halo (preferably bromo), tosylate, mesylate, or other alkyl or aryl sulfonate esters;
(k) multifunctional aldehydes, for example, glutaraldehyde, trioxane, paraformaldehyde, terephthaldehyde, malonaldehyde, and glyoxal, and acetals and bisulfites thereof;
(l) multifunctional carboxylic acids and esters, acid chlorides, and anhydrides derived therefrom, for example, di- and polycarboxylic acids containing 2 to 12 carbon atoms, and the methyl and ethyl esters, acid chlorides, and anhydrides derived therefrom, such as oxalic acid, adipic acid, succinic acid, dodecanoic acid, malonic acid, and glutaric acid, and esters, anhydrides, and acid chlorides derived therefrom;
(m) organic titanates, such as TYZOR AA, available from E.I. DuPont de Nemours, Wilmington, Del.;
(n) melamine resins, such as the CYMEL resins available from Cytec Industries, Wayne, N.J.;
(o) hydroxymethyl ureas, such as N,N'-dihydroxymethyl-4,5-dihydroxyethylene urea;
(p) a hydroxyalkylamide (HAA), for example, as disclosed in U.S. Pat. No. 6,239,230, incorporated herein by reference, but not limited to, bis[N,N-di(β-hydroxyethyl)]adipamide, bis[N,N-di(β-hydroxypropyl)]succinamide, bis[N,N-di(β-hydroxyethyl)]azelamide, bis[N-N-di(β-hydroxypropyl)]adipamide, and bis[N-methyl-N-(β-hydroxyethyl)] oxamide. A commercially available β-HAA is PRIMID™ XL-552 from EMS-CHEMIE, Dornat, Switzerland. Another commercially available HAA is PRIMID™ QM-1260 from EMS-CHEMIE;
(q) 2-oxazolidinone and its derivatives; and
(r) other crosslinking agents for SAPs known to persons skilled in the art.

A preferred surface crosslinking agent comprises an HAA, ethylene glycol diglycidyl ether (EGDGE), propylene glycol, or mixtures thereof.

It is theorized, but not relied upon herein, that inhibitors, which are added to the vinyl monomers to prevent premature polymerization during transport and storage, and which are present in the SAP polymer, are slowly oxidized by a persulfate causing the color of the SAP to degrade from white to honey brown. This color change occurs at a faster rate at elevated temperatures and relative humidity.

For example, the monomethyl ether of hydroquinone (MEHQ) is the inhibitor typically used to prevent the premature polymerization of acrylic monomers used in the manufacture of the SAPs, like acrylic acid and the crosslinking agents. Typically, the amount of inhibitor, like MEHQ, added to the monomer is about 15 to about 200 ppm. The inhibitors are not consumed during polymerization and are present in the SAP hydrogel after polymerization of the monomers. The color change of the SAP is theorized to result from oxidation of an inhibitor, like MEHQ, by a persulfate to a quinone.

To prevent color degradation of an SAP to a consumer-unacceptable honey brown color, a monomer mixture used to provide an SAP is essentially free of a persulfate, and about 10 to about 50 ppm of a photoinitiator is included in the monomer mixture. By using a monomer mixture essentially free of a persulfate, the resulting SAP has a crisp, white color, and the white color of the resulting SAP is stabilized and preserved. The photoinitiator is present in the monomer mixture to assist in reducing the amount of free monomer in the SAP. Free monomer reduction is achieved by subjecting an SAP hydrogel to a low dose of UV radiation after polymerization of the monomer mixture and before comminution of the SAP hydrogel.

Therefore, the present invention is directed to a method of manufacturing an SAP that improves the color, and avoids discoloration, of SAPs. Typically, in current modified bulk polymerization processes, a preneutralized monomer solution is polymerized using a thermal azo initiator (e.g., V-50) and sodium persulfate as initiators on a belt conveyor. The temperature of the monomer solution initially is about 60° C. Due to the heat of polymerization, a substantial portion of the water of the monomer mixture evaporates, and the final solids content of the SAP hydrogel is about 85 wt %, i.e., about 15% water, before drying. The interaction between sodium persulfate and the MEHQ inhibitor results in a low initial SAP color and additional SAP discoloration during storage, especially under hot and humid conditions. To date, sodium persulfate has been an important, or a necessary, ingredient in the monomer mixture to reduce the residual acrylic acid content in the SAP to a consumer-acceptable level.

It now has been found that the monomer mixture can be essentially free of a persulfate, and a redox and/or thermal initiator, in combination with a photoinitiator and UV radiation dose, can be used to reduce residual acrylic acid in a color-stable SAP. In the present process, a low dose of UV radiation is administered at the end of a modified bulk polymerization process, i.e., after a majority of the acrylic acid monomer has been converted to an SAP hydrogel and the water content of the gel has been reduced to about 25 wt % or less. In accordance with the present invention, unexpectedly low residual acrylic acid levels are achieved and the initial color and long-time color of the SAP are improved considerably.

In particular, a monomer mixture is formed by admixing the monomers, crosslinking agent, polymerization initiators, photoinitiator, and water. Although the order of admixing these materials is not particularly important, it is preferred to add the initiators last for safety reasons. The amounts of the individual components of the monomer mixture are set forth above.

The monomer mixture then is subjected to conditions under which the monomers and crosslinking agents polymerize to form an SAP hydrogel containing about 25 wt % or less water. Ultraviolet radiation is not used to facilitate the polymerization reaction. The conditions can be continuous, such as by applying the monomer mixture to a moving conveyor that passes through a heating zone that initiates the polymerization reaction. In this embodiment, one or more polymerization initiator can be omitted from the monomer mixture and added to the monomer mixture after application to the conveyor.

After polymerization on the conveyor, the resulting SAP hydrogel advances to a UV zone, wherein a low dose of UV radiation is applied to the SAP hydrogel. The SAP hydrogel then is subjected to a mechanical comminution, i.e., reduction of the SAP hydrogel to SAP hydrogel particles, for example, by chopping.

The SAP hydrogel, if not previously neutralized, can be neutralized with a base, for example, with sodium carbonate, to provide an SAP hydrogel having a degree of neutralization (DN) of about 50 to about 100, preferably about 65 to about 85, more preferably about 75 to about 80. Preferably, the monomers are neutralized prior to polymerization.

After UV irradiation, drying of the SAP hydrogel provides a color-stable SAP of the present invention. Drying is performed by methods well known in the art, for example, using a fluidized bed dryer, a band dryer, or similar industrial dryer. The dried SAP optionally then is surface crosslinked with a surface crosslinker, like ethylene glycol diglycidyl ether (i.e., "EGDGE") or an HAA, for example.

The SAP hydrogel is subjected to a low dose of UV radiation intensity, for example, about 2000 milliwatt/cm$^2$ or less, preferably 500 milliwatt/cm$^2$ or less, and to achieve the full advantage of the present invention, about 5 up to about 100 milliwatt/cm$^2$.

The UV radiation dose generally is administered using a UV lamp with an intensity of about 100 to about 700 watts per inch (W/in), preferably about 400 to about 600 W/in, for 0.1 seconds to 60 minutes, with the distance between the UV lamp and the SAP hydrogel preferably being 2 to 30 centimeters. UV radiation can be conducted under vacuum, in the presence of an inorganic gas, such as nitrogen, argon, helium, and the like, or in air. Suitable UV sources include a UV flood system from Stama or a Solartell Solarscope, Model 1, with a multidirectional probe.

Particles of a color-stable SAP of the present invention can be in any form, either regular or irregular, such as granules, fibers, beads, powders, flakes, or foams, or any other desired shape, such as a sheet. In embodiments wherein the color-stable SAP is prepared using an extrusion step, the shape of the SAP is determined by the shape of the extrusion die. The shape of the color-stable SAP particles also can be determined by other physical operations, such as milling.

In one embodiment, the particles of the color-stable SAP are in the form of a granule or a bead, having a particle size of about 10 to about 10,000 microns (µm), and preferably about 100 to about 1,000 µm. To achieve the full advantage of the present invention, the particles of the color-stable SAP have a particle size of about 150 to about 800 µm.

In another embodiment, the particles of the color-stable SAP are in the shape of a fiber, i.e., an elongated, acicular particle. The fiber can be in the shape of a cylinder, for example, having a minor dimension (i.e., diameter) and a major dimension (i.e., length). The fiber also can be in the form of a long filament that can be woven. Such filament-like fibers have a weight of below about 80 decitex, and preferably below about 70 decitex, per filament, for example, about 2 to about 60 decitex per filament. Tex is the weight in grams per one kilometer of fiber. One tex equals 10 decitex. Polyacrylic acid is about 4 decitex.

Cylindrical fibers of a color-stable SAP have a minor dimension (i.e., diameter of the fiber) less than about 1 mm, usually less than about 500 µm, and preferably less than 250 µm, down to about 50 µm. The cylindrical fibers can have a relatively short major dimension, for example, about 1 mm, e.g., in a fibrid, lamella, or flake-shaped article, but generally the fiber has a length of about 3 to about 100 mm. The filament-like fibers have a ratio of major dimension to minor dimension of at least 500 to 1, and preferably at least 1000 to 1, for example, up to and greater than 10,000 to 1.

The method of the present invention also can be used in the preparation of a multicomponent SAP, as disclosed in U.S. Pat. Nos. 6,072,101; 6,159,591; 6,222,091; and 6,329,062, each incorporated herein by reference.

A color-stable SAP of the present invention has an outstanding water-absorbing ability, and is useful for use in sanitary goods, paper diapers, disposable diapers and similar hygienic goods, agricultural or horticultural water-retaining agents, industrial dehydrating agents, sludge coagulants, thickening agents, condensation preventing agents for building materials, release control agents for chemicals and various other applications. Furthermore, a present color-stable SAP retains its white color over extended storage periods at elevated temperature and relative humidity. The present color-stable SAP particles, therefore, are useful in articles, like diapers, having improved consumer appeal.

After storage at 60° C. and 90% relative humidity for 30 days, a color-stable SAP of the present invention exhibits an HC60 color value of at least about 60, and preferably at least about 63. To achieve the full advantage of the present invention, the SAP exhibits an HC60 color value of at least about 65 after storage at 60° C. and 90% relative humidity for 30 days.

Furthermore, after storage at 60° C. and 90% relative humidity for 30 days, a color-stable SAP of the present invention exhibits a maximum b-value of 10, and preferably a maximum of 8. To achieve the full advantage of the present invention, the SAP exhibits a b-value maximum of 7 after storage at 60° C. and 90% relative humidity for 30 days.

EXAMPLES

The following illustrate nonlimiting examples of the present invention, and are not intended to limit the scope thereof.

Test Methods

Centrifuge Retention Capacity (CRC)

The CRC (centrifuge retention capacity) test is designed to measure the amount of 0.9% saline solution retained inside an SAP when under a specific centrifuge force. Measurement of CRC is disclosed in U.S. Pat. No. 6,187,828 and U.S. Pat. No. 5,633,316, each incorporated herein by reference.

Absorbency Under Load (AUL)

The AUL (absorbency under load) test is designed to measure the ability of an SAP to absorb a fluid under load. Measurement of AUL is disclosed in U.S. Pat. No. 6,187,828 and U.S. Pat. No. 5,633,316, each incorporated herein by reference.

Residual Acrylic Acid

One gram of SAP is weighed into a 250 mL beaker. A 0.9% saline solution (200 ml) and a stir bar are placed in the beaker, the beaker is covered with parafilm, then the mixture is stirred at 500 rpm for 1 hour. After 1 hour, the sample is allowed to settle for 5 minutes, then the supernatant is filtered using a 3 cc sterile syringe and 0.45 µm filter. The content of acrylic acid is measured by HPLC analysis using 0.1 N sulfuric acid as mobile phase and UV detection (210 nm).

Hunter Color (HC60) and b-value

This test procedure is a method of measuring the perceived color of polymer related to its spectral characteristics. Spectral characteristics are specified by reflectance (or transmittance) as a function of wavelength. The measurement is performed on the polymer powder with a MACBETH Color-Eye 2180 Spectrophotometer according to the manufacturer's instructions, using a reflection cuvette or 35×10 mm petri dish with lid as sample cell.

In this system, "L" is a measure of the lightness of a sample, and ranges from 0 (black) to 100 (white); and "b" is a measure of yellowness (positive b-values) or blueness (negative b-values).

Hunter Color HC60 is defined as:

$HC60=L-3b.$

Example 1

Acrylic acid (92.4 g), 0.026 g trimethylolpropane triacrylate, and 87.2 g demineralized water were admixed. Sodium carbonate (40.4 g) was added, and the temperature of the monomer solution was maintained below 30° C. during the neutralization reaction. Then, 0.081 g 2,2'-azobisamidinopropane dihydrochloride, 0.018 g DAROCUR® 1173, and 0.040 g hydrogen peroxide were admixed into the monomer mixture. The monomer mixture was heated to 62° C. and poured into a pan, then 0.015 g sodium sulfite, dissolved in 5 g demineralized water, was added to initiate the polymerization. Due to the heat of polymerization, the major part of the water evaporated during the reaction, and at the end of the polymerization, a polymer mass having a residual moisture content of about 15 wt. % was obtained. The polymer mass was placed under UV light (UV intensity=20 mW/cm$^2$) for 8 minutes, then dried in a drying oven at 120° C., milled, and classified to a particle size distribution 106-850 μm. The dry powder then was surface crosslinked by spraying a solution containing of 0.12 wt. % ethylene glycol diglycidyl ether based on powder, 3.35 wt. % water based on powder, and 1.65 wt. % isopropanol based on powder onto the powder particles, followed by quring at 150° C. for one hour. The properties of the resulting polymer were as follows:

| | |
|---|---|
| CRC = | 29.8 g/g |
| AUL 0.7 psi = | 23.5 g/g |
| Residual acrylic acid = | 50 ppm |
| Hunter Color, HC60, initial = | 87 |
| Hunter Color, HC60, after 30 days @60° C./90% relative humidity = | 69 |
| Hunter Color, b-value, initial = | 2.4 |
| Hunter Color, b-value, after 30 days @60° C./90% relative humidity = | 4.6 |

Example 2

Acrylic acid (29.4 g), 0.04 g tetraallyl ammonium chloride, and 87.2 g demineralized water were admixed. Sodium carbonate (40.4 g) was added, and the temperature of the monomer solution was maintained below 30° C. during the neutralization reaction. Then, 0.081 g 2,2'-azobisamidinopropane dihydrochloride, 0.018 g DAROCUR® 1173, and 0.040 g hydrogen peroxide were admixed into the monomer mixture. The monomer mixture was heated to 62° C. and poured into a pan, then 0.018 g 2-hydroxy-2-sulfinatoacetic acid, disodium salt (BRUGGOLITE® FF7, commercially available from Bruggemann Chemical), dissolved in 5 g demineralized water, was added to initiate the polymerization. Due to the heat of polymerization, the major part of the water evaporated during the reaction, and at the end of the polymerization, a polymer mass having a residual moisture content of about 15 wt. % was obtained. The polymer mass was placed under UV light (UV intensity=20 mW/cm$^2$) for 12 minutes, then dried in a drying oven at 120° C., milled, and classified to a particle size distribution 106-850 μm. The dry powder then was surface crosslinked by spraying a solution containing 0.15 wt. % ethylene glycol diglycidyl ether based on powder, 3.35 wt. % water based on powder, and 1.65 wt. % 1,2-propylene glycol based on powder onto the powder particles, followed by curing at 150° C. for one hour. The properties of the resulting polymer were as follows:

| | |
|---|---|
| CRC = | 28.2 g/g |
| AUL 0.7 psi = | 24.2 g/g |
| Residual acrylic acid = | 20 ppm |
| Hunter Color, HC60, initial = | 86 |
| Hunter Color, HC60, after 30 days @60° C./90% relative humidity = | 68 |
| Hunter Color, b-value, initial = | 2.3 |
| Hunter Color, b-value, after 30 days @60° C./90% relative humidity = | 4.5 |

Comparative Example 1

Acrylic acid (92.4 g), 0.026 g trimethylolpropane triacrylate, and 87.2 g demineralized water were admixed. Sodium carbonate (40.4 g) was added, and the temperature of the monomer solution was maintained below 30° C. during the neutralization reaction. Then, 0.081 g 2,2'-azobisamidinopropane dihydrochloride and 0.15 g sodium persulfate were admixed into the monomer mixture. The monomer mixture was poured into a pan and heated to 67° C. to initiate the polymerization. Due to the heat of polymerization, the major part of the water evaporated during the reaction, and at the end of the polymerization, a polymer mass having a residual moisture content of about 13 wt. % was obtained. The polymer mass was dried in a drying oven at 120° C., milled, and classified to a particle size distribution 106-850 μm. The dry powder then was surface crosslinked by spraying a solution containing 0.12 wt. % ethylene glycol diglycidyl ether based on powder, 3.35 wt. % water based on powder, and 1.65 wt. % isopropanol based on powder onto the powder particles, followed by curing at 150° C. for one hour. The properties of the resulting polymer were as follows:

| | |
|---|---|
| CRC = | 32.3 g/g |
| AUL 0.7 psi = | 20.8 g/g |
| Residual acrylic acid = | 175 ppm |
| Hunter Color, HC60, initial = | 65 |
| Hunter Color, HC60, after 30 days @60° C./90% relative humidity | 22 |
| Hunter Color, b-value, initial = | 7.9 |
| Hunter Color, b-value, after 30 days @60° C./90% relative humidity = | 14.5. |

Comparative Example 2

Acrylic acid (92.4), 0.026 g trimethylolpropane triacrylate, and 87.2 g demineralized water were admixed. Sodium carbonate (40.4 g) was added, and the temperature of the monomer solution was maintained below 30° C. during the neutralization reaction. Then, 0.081 g 2,2'-azobisamidinopropane dihydrochloride, 0.018 g DAROCUR® 1173, and 0.040 g hydrogen peroxide were admixed into the monomer mixture. The monomer mixture was heated to 62° C. and poured into a pan, then 0.015 g sodium sulfite, dissolved in 5 g demineralized water, was added to initiate the polymerization. Due to the heat of polymerization, the major part of the water evaporated during the reaction, and at the end of the polymerization, a polymer mass having a residual moisture content of about 15 wt. % was obtained. The polymer mass was dried in an oven at 120° C., milled, and classified to a particle size distribution 106-850 μm. The dry powder then was surface crosslinked by spraying a solution containing 0.12 wt. % ethylene glycol diglycidyl ether based on powder, 3.35 wt. % water based on powder, and 1.65 wt. % isopropanol based on powder onto the powder particles, followed by curing at 150° C. for one hour. The properties of the resulting polymer were as follows:

| | |
|---|---|
| CRC = | 30.3 g/g |
| AUL 0.7 psi = | 22.7 g/g |
| Residual acrylic acid = | 890 ppm |
| Hunter Color, HC60, initial = | 85 |
| Hunter Color, HC60, after 30 days @60° C./90% relative humidity = | 66 |
| Hunter Color, b-value, initial = | 2.3 |
| Hunter Color, b-value, after 30 days @60° C./90% relative humidity = | 5.1. |

Comparative Example 3

Acrylic acid (73.9 g), 0.032 9 tetraallyl ammonium chloride, and 87.2 g demineralized water were admixed. Sodium carbonate (32.3 g) was added, and the temperature of the monomer solution was maintained below 30° C. during the neutralization reaction. Then, 0.081 g 2,2'-azobisamidinopropane dihydrochloride, 0.018 g DAROCUR® 1173, and 0.040 g hydrogen peroxide were admixed into the monomer mixture. The monomer mixture was heated to 62° C. and poured into a pan, then 0.018 g 2-hydroxy-2-sulfinatoacetic acid, disodium salt (BRUGGOLITE® FF7), dissolved in 5 g demineralized water, was added to initiate the polymerization. Due to the heat of polymerization, a part of the water evaporated during the reaction, and at the end of the polymerization, a polymer mass having a residual moisture content of about 33 wt. % was obtained. The polymer mass was placed under UV light (UV intensity=20 mW/cm$^2$) for 12 minutes, then dried in a drying oven at 120° C., milled and classified to a particle size distribution 106-850 μm. The dry powder then was surface crosslinked by spraying a solution containing 0.15 wt. % ethylene glycol diglycidyl ether based on powder, 3.35 wt. % water based on powder, and 1.65 wt. % 1,2-propylene glycol based on powder onto the powder particles, followed by curing at 150° C. for one hour. The properties of the resulting polymer were as follows:

| | |
|---|---|
| CRC = | 29.7 g/g |
| AUL 0.7 psi = | 22.9 g/g |
| Residual acrylic acid = | 970 ppm |
| Hunter Color, HC60, initial = | 88 |
| Hunter Color, HC60, after 30 days @60° C./90% relative humidity = | 68 |
| Hunter Color, b-value, initial = | 2.1 |
| Hunter Color, b-value, after 30 days @60° C./90% relative humidity = | 4.9. |

As shown in Comparative Example 3, it was found that the reduction of residual acrylic acid monomer in the SAP is related to the moisture content of the SAP hydrogel. At a lower SAP hydrogel water content (e.g., 20% or less), it is theorized, but not relied upon, that the mobility of the polymer chains is restricted. Therefore, the formed radicals have a longer lifetime and more efficiently react with, and eliminate, residual acrylic acid. To achieve a sufficient reduction in the residual acrylic acid, the SAP hydrogel has a water content of less than 25%, by weight, when subjected to UV radiation. Preferably, the SAP hydrogel, prior to UV radiation, has a water content of about 10% to less than 25%, and more preferably about 10% to about 20%.

Overall, it has been found that essentially eliminating a persulfate, and including about 10 to about 1000 ppm of a photoinitiator, in the monomer mixture, and irradiating the resulting SAP hydrogel with a low dose of UV radiation provides an SAP manufacturing process for a color-stable SAP. The method applies to both preneutralization and post-neutralization SAP manufacturing processes. The color-stable SAP maintains a crisp, white color over extended storage periods, including in high temperature and humidity storage conditions.

Many modifications and variations of the invention as hereinbefore set forth can be made without departing from the spirit and scope thereof and, therefore, only such limitations should be imposed as are indicated by the appended claims.

What is claimed is:

1. A method of manufacturing color-stable superabsorbent polymer particles comprising the steps of:
   (a) forming a monomer mixture comprising:
      (i) at least one monomer capable of forming a superabsorbent polymer,
      (ii) a crosslinking agent,
      (iii) an initiator system that contains 0 to 300 ppm of a persulfate;
      (iv) a photoinitiator, and
      (v) optionally water;
   (b) polymerizing the monomer and the crosslinking agent in the monomer mixture to form a superabsorbent polymer hydrogel having a water content of 25 wt.% or less;
   (c) subjecting the superabsorbent polymer hydrogel to a UV radiation of 2000 milliwatt/cm$^2$ or less;
   (d) then comminuting the superabsorbent polymer hydrogel to provide superabsorbent hydrogel particles; and
   (e) drying the superabsorbent polymer hydrogel particles for a sufficient time at a sufficient temperature to provide the color-stable superabsorbent polymer particles.

2. The method of claim 1 wherein the initiator system comprises a redox initiator.

3. The method of claim 1 wherein the initiator system further comprises a thermal initiator.

4. The method of claim 2 wherein the redox initiator comprises hydrogen peroxide as an oxidizing agent.

5. The method of claim 2 wherein the redox initiator comprises 2-hydroxy-2-sulfinatoacetic acid, a sulfite, a bisulfite, or a mixture thereof as a reducing agent.

6. The method of claim 1 wherein the superabsorbent polymer hydrogel in step (b) contains 10% to 25%, by weight, water.

7. The method of claim 1 wherein the superabsorbent polymer hydrogel in step (c) is subjected to 5 to 2000 milliwatts of radiation per square centimeter of the superabsorbent polymer hydrogel.

8. The method of claim 1 wherein the photoinitiator is present in the monomer mixture in an amount of 10 to 1000 ppm, by weight, of the monomer mixture.

9. The method of claim 1 wherein the photoinitiator comprises a compound having a formula

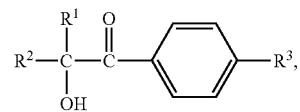

wherein $R^1$ and $R^2$, independently, are $C_{1-3}$alkyl, or are taken together to form a $C_{4-8}$carbocyclic ring, $R^3$ is H, methyl, ethyl, or $(OCH_2CH_2)_n OH$, and n is 1-20.

10. The method of claim 1 wherein the photoinitiator comprises hydroxycyclohexyl phenyl ketone, 2,2-dimethoxy-1,2-diphenylethan-1-one,

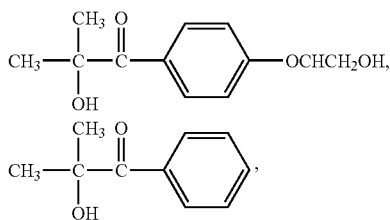

or a mixture thereof.

11. The method of claim 1 wherein the photoinitiator comprises benzoin, a benzoin ether, a benzyl ketal, an acylphosphine oxide, comphorquinone, bisimidazole, a dialkylacetophenone, an α-aminoacetophenone, a chlorinated acetophenone, benzophenone, a benzophenone derivative, p-benzoylbenzyl trimethyl ammonium bromide, a thioxanthone derivative, (3-(3,4-dimethyl-9-oxo-9H-thioxanthen-2-yloxy)-2-hydroxypropyl)trimethyl ammonium chloride, and mixtures thereof.

12. The method of claim 1 wherein the superabsorbent polymer particles comprise a polymerized α,β-unsaturated carboxylic acid, or a salt or anhydride thereof.

13. The method of claim 1 wherein the monomer capable of forming the superabsorbent polymer is selected from the group consisting of acrylic acid, methacrylic acid, ethacrylic acid, α-chloroacrylic acid, α-cyanoacrylic acid, β-methylacrylic acid, α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, maleic anhydride, vinylsulfonic acid, allylsulfonic acid, vinyl toluenesulfonic acid, styrenesulfonic acid, sulfoethyl acrylate, sulfoethyl methacrylate, sulfopropyl acrylate, sulfopropyl methacrylate, 2-hydroxy-3-methacryloxypropyl sulfonic acid, 2-acrylamido-2-methylpropane sulfonic acid, methacryloxy ethyl phosphate, and mixtures thereof.

14. The method of claim 1 wherein the superabsorbent polymer is selected from the group consisting of polyacrylic acid, a hydrolyzed starch-acrylonitrile graft copolymer, a starch-acrylic acid graft copolymer, a hydrolyzed acrylonitrile copolymer, a hydrolyzed acrylamide copolymer, an ethylene-maleic anhydride copolymer, an isobutylene-maleic anhydride copolymer, a poly(vinylsulfonic acid), a poly(vinylphosphonic acid), a poly(vinylphosphoric acid), a poly(vinylsulfuric acid), a sulfonated polystyrene, and salts and mixtures thereof.

15. The method of claim 1 wherein the superabsorbent polymer comprises polyacrylic acid neutralized 15% to 100%.

16. The method of claim 1 wherein the superabsorbent polymer is selected from the group consisting of a poly(vinylamine), a poly(dialkylaminoalkyl(meth)acrylamide), a polyethylenimine, a poly(allylamine), a poly(allylguanidine), a poly(dimethyldiallylammonium hydroxide), a quaternized polystyrene derivative, a guanidine-modified polystyrene, a quaternized poly((meth)acrylamide) or ester analog, a poly(vinylguanidine), and salts and mixtures thereof.

17. The method of claim 1 wherein the superabsorbent polymer comprises a multicomponent superabsorbent polymer.

18. The method of claim 1 wherein the color-stable superabsorbent polymer particles, after storage for 30 days at 60° C. and 90% relative humidity, exhibit an HC60 color value of at least 60.

19. The method of claim 1 wherein the color-stable superabsorbent polymer particles, after a storage for 30 days at 60° C. and 90% relative humidity, exhibit a maximum b-value of 10.

20. The method of claim 1 wherein the color-stable superabsorbent polymer particles have a residual monomer content of 500 ppm or less.

21. The method of claim 1 wherein the monomer comprises acrylic acid; the initiator system consists essentially of hydrogen peroxide as an oxidizing agent, 2-hydroxy-2-sulfinatoacetic acid, a sulfite, a bisulfite, or a mixture thereof as a reducing agent, and a thermal initiator; the photoinitiator is present in an amount of 15 to 1000 ppm, by weight, of the monomer mixtures; and the superabsorbent polymer hydrogel of step (b) contains 15% to 20% by weight water and is subjected to 5 to 2000 milliwatts of radiation per square centimeter of the superabsorbent polymer hydrogel.

22. The method of claim 1 further comprising the step of:
(f) surface treating the color-stable superabsorbent polymer particles.

23. Surface treated color-stable superabsorbent polymer particles wherein the polymer particles, after storage for 30 days at 60° C. and 90% relative humidity, exhibit an HC60 color value of at least 63 and a maximum b-value of 10.

24. An absorbent article comprising the color-stable superabsorbent polymer particles according to claim 23.

25. The article of claim 24 wherein the article is a diaper or a catamenial device.

26. A diaper having a core, said core comprising at least 10% by weight of the color-stable superabsorbent polymer particles according to claim 23.

27. The diaper of claim 26 wherein the core comprises at least 25% by weight of the color-stable superabsorbent polymer particles.

* * * * *